(12) United States Patent
Kari et al.

(10) Patent No.: US 7,150,758 B2
(45) Date of Patent: Dec. 19, 2006

(54) KINK RESISTANT ENDOVASCULAR GRAFT

(75) Inventors: Stuart E Kari, Windsor, CA (US); Michael V. Chobotov, Santa Rosa, CA (US)

(73) Assignee: Boston Scientific Santa Rosa Corp., Santa Rosa, CA (US)

( * ) Notice: Subject to any disclaimer, the term of this patent is extended or adjusted under 35 U.S.C. 154(b) by 0 days.

(21) Appl. No.: 10/384,103

(22) Filed: Mar. 6, 2003

(65) Prior Publication Data

US 2004/0176836 A1 Sep. 9, 2004

(51) Int. Cl.
*A61F 2/06* (2006.01)

(52) U.S. Cl. .................................................. 623/1.25

(58) Field of Classification Search ...... 623/1.15–1.35; 604/509, 99.04
See application file for complete search history.

(56) References Cited

U.S. PATENT DOCUMENTS

| | | | |
|---|---|---|---|
| 3,631,854 A | 1/1972 | Fryer | |
| 3,902,198 A | 9/1975 | Rathjen | |
| 3,991,767 A | 11/1976 | Miller, Jr. et al. | |
| 4,183,102 A | 1/1980 | Guiset | |
| 5,151,105 A | 9/1992 | Kwan-Gett | |
| 5,156,620 A | 10/1992 | Pigott | |
| 5,330,528 A | 7/1994 | Lazim | |
| 5,370,691 A | 12/1994 | Samson | |
| 5,411,550 A | 5/1995 | Herweck et al. | |
| 5,529,653 A | 6/1996 | Glastra | |
| 5,534,024 A | 7/1996 | Rogers et al. | |
| 5,554,180 A | 9/1996 | Turk | |
| 5,556,426 A | 9/1996 | Popadiuk et al. | |
| 5,607,468 A | 3/1997 | Rogers et al. | |
| 5,607,478 A | 3/1997 | Lentz et al. | |
| 5,609,624 A | 3/1997 | Kalis | |
| 5,665,117 A | 9/1997 | Rhodes | |
| 5,709,701 A | 1/1998 | Parodi | |
| 5,749,880 A | 5/1998 | Banas et al. | |
| 5,871,537 A | 2/1999 | Holman et al. | |
| 5,976,179 A | 11/1999 | Inoue | |
| 6,007,575 A | 12/1999 | Samuels | |
| 6,042,605 A | 3/2000 | Martin et al. | |
| 6,053,943 A | 4/2000 | Edwin et al. | |
| 6,059,823 A | 5/2000 | Holman et al. | |
| 6,132,457 A | 10/2000 | Chobotov | |
| 6,143,015 A | 11/2000 | Nobles | |
| 6,235,050 B1 * | 5/2001 | Quiachon et al. | ........... 623/1.11 |
| 6,293,968 B1 | 9/2001 | Taheri | |
| 6,312,462 B1 * | 11/2001 | McDermott et al. | ........ 623/1.25 |
| 6,331,191 B1 | 12/2001 | Chobotov | |

(Continued)

FOREIGN PATENT DOCUMENTS

EP 617 930 10/1994

(Continued)

OTHER PUBLICATIONS

Haimovitch et al., "Robust growth is forecast for endovascular repair of AAAs," *The BBI Newsletter*, 26(5):113-114 (May 2003).

(Continued)

*Primary Examiner*—Corrine McDermott
*Assistant Examiner*—William H Matthews
(74) *Attorney, Agent, or Firm*—Hoffmann & Baron, LLP

(57) ABSTRACT

An intracorporeal device, such as an endovascular graft, having a tubular section with circumferential or helical radial support members. The radial support members may be inflatable channels which support the tubular structure of the graft and which are appropriately sized and longitudinally spaced to prevent or reduce kinking of the tubular structure upon bending of the tubular structure.

41 Claims, 5 Drawing Sheets

U.S. PATENT DOCUMENTS

| | | |
|---|---|---|
| 6,361,637 B1 | 3/2002 | Martin et al. |
| 6,371,979 B1 * | 4/2002 | Beyar et al. ............... 623/1.12 |
| 6,395,019 B1 | 5/2002 | Chobotov |
| 6,398,803 B1 | 6/2002 | Layne et al. |
| 6,416,537 B1 | 7/2002 | Martakos et al. |
| 6,524,334 B1 | 2/2003 | Thompson |
| 6,602,280 B1 | 8/2003 | Chobotov |
| 2001/0007955 A1 | 7/2001 | Drasler et al. |
| 2001/0049550 A1 | 12/2001 | Martin et al. |
| 2002/0002397 A1 | 1/2002 | Martin et al. |
| 2002/0099436 A1 | 7/2002 | Thornton et al. |
| 2002/0151953 A1 | 10/2002 | Chobotov et al. |
| 2002/0151956 A1 | 10/2002 | Chobotov et al. |
| 2002/0165603 A1 | 11/2002 | Thornton et al. |
| 2002/0173836 A1 | 11/2002 | Pinchuk |
| 2003/0004560 A1 | 1/2003 | Chobotov et al. |
| 2003/0040803 A1 * | 2/2003 | Rioux et al. ............... 623/23.7 |
| 2003/0074048 A1 | 4/2003 | Sherry |
| 2003/0074058 A1 | 4/2003 | Sherry |
| 2003/0093145 A1 | 5/2003 | Lawrence-Brown et al. |
| 2003/0116260 A1 | 6/2003 | Chobotov et al. |
| 2003/0120331 A1 * | 6/2003 | Chobotov et al. ......... 623/1.13 |
| 2003/0120338 A1 * | 6/2003 | Chobotov et al. ......... 623/1.36 |
| 2003/0125797 A1 | 7/2003 | Chobotov et al. |
| 2003/0220681 A1 | 11/2003 | Chobotov |
| 2005/0209580 A1 * | 9/2005 | Freyman ..................... 604/509 |

FOREIGN PATENT DOCUMENTS

| | | |
|---|---|---|
| EP | 441 516 | 3/1995 |
| WO | WO 98/55047 | 12/1998 |
| WO | WO 99/00073 | 1/1999 |
| WO | WO 99/26559 | 6/1999 |
| WO | WO 99/39662 | 6/1999 |
| WO | WO 99/32051 | 7/1999 |
| WO | WO 00/51522 | 9/2000 |
| WO | WO 01/21107 | 3/2001 |
| WO | WO 02/29758 | 4/2002 |

OTHER PUBLICATIONS

Uflacker, R. and Robinson, J., "Endovascular treatment of abdominal aortic aneurysms: a review," *Eur. Radial.*, 11:739-753 (2001).
US 6,413,270, 07/2002, Thornton et al. (withdrawn)

* cited by examiner

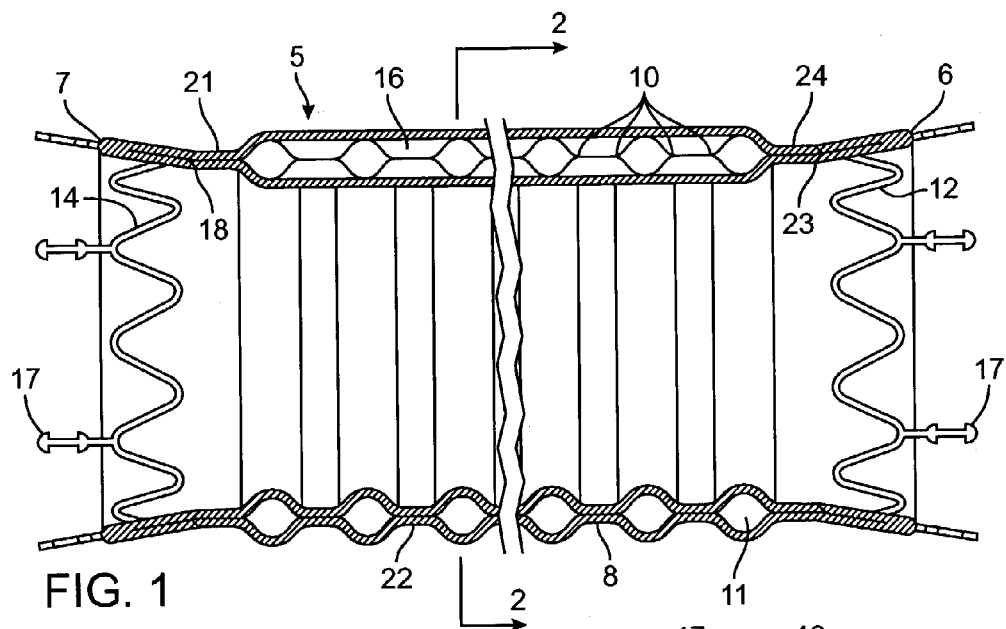
FIG. 1
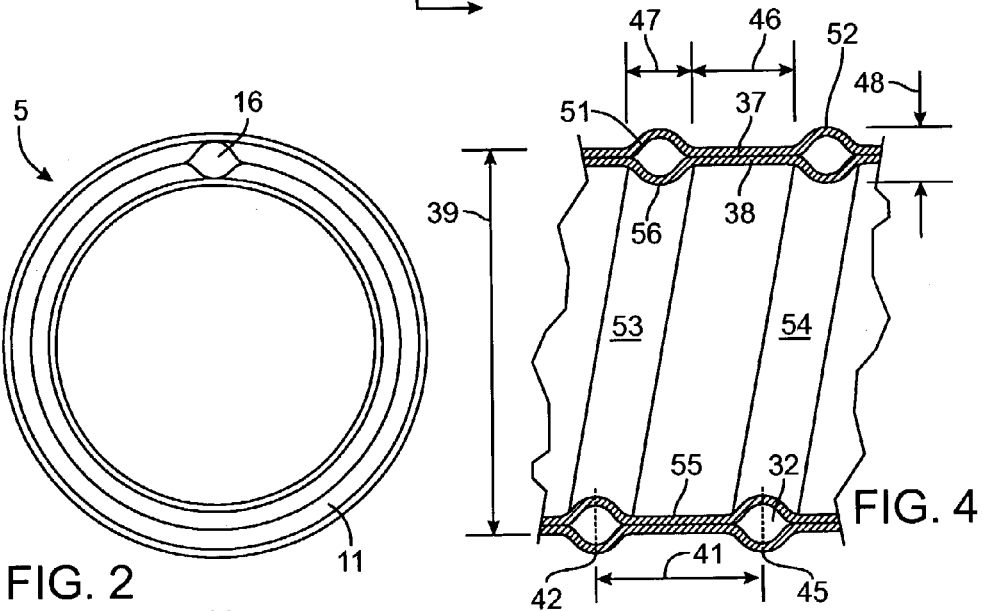
FIG. 2
FIG. 4
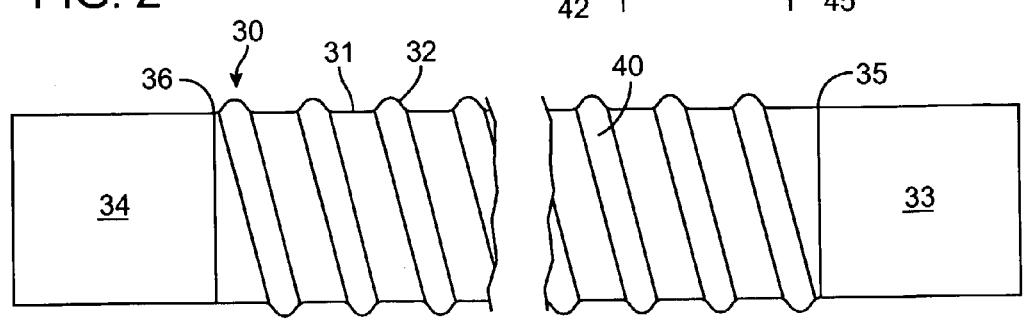
FIG. 3

KINK RESISTANT ENDOVASCULAR GRAFT

BACKGROUND OF THE INVENTION

Embodiments of the device and method discussed herein relate to a system and method for manufacturing intracorporeal devices used to replace, strengthen, or bypass body channels or lumens of patients; in particular, those channels or lumens, such as the abdominal or thoracic aorta, that have been affected by conditions such as aneurysmal disease.

Existing methods of treating such aneurysms include invasive surgical methods with graft placement within the aorta as a reinforcing member of the artery. Although improvements in surgical and anesthetic techniques have reduced perioperative and postoperative morbidity and mortality, significant risks associated with surgical repair (including myocardial infarction and other complications related to coronary artery disease) still remain.

Due to the inherent hazards and complexities of such surgical procedures, various attempts have been made to develop alternative repair methods that involve the endovascular deployment of grafts within aortic aneurysms. One such method is the non-invasive technique of percutaneous delivery of grafts and stent-grafts by a catheter-based system. Such a method is described by Lawrence, Jr. et al. in "Percutaneous Endovascular Graft: Experimental Evaluation", *Radiology* (1987). Lawrence et al. describe therein the use of a Gianturco stent as disclosed in U.S. Pat. No. 4,580,568 to Gianturco. The stent is used to position a Dacron® fabric graft within the vessel. The Dacron® graft is compressed within the catheter and then deployed within the vessel to be treated.

A similar procedure is described by Mirich et al. in "Percutaneously Placed Endovascular Grafts for Aortic Aneurysms: Feasibility Study,"*Radiology* (1989). Mirich et al. describe therein a self-expanding metallic structure covered by a nylon fabric, the structure being anchored by barbs at the proximal and distal ends.

An improvement to percutaneously delivered grafts and stent-grafts results from the use of materials such as polytetrafluoroethylene (PTFE) and expanded polytetrafluoroethylene (ePTFE) for a graft body. These and similar materials have clinically beneficial properties. However, endovascular grafts and other devices made from material such as PTFE and ePTFE can be susceptible to kinking due to, among other reasons, the flexibility and pliability of these materials. What is needed is an endovascular graft that provides the advantages of construction from these materials but that is resistant to kinking and other types of deformation that may be detrimental to graft performance.

BRIEF SUMMARY OF THE INVENTION

Embodiments of the invention are directed to configurations of tubular or bifurcated intracorporeal structures and devices, such as endovascular grafts and stent-grafts, which have radial support member configurations that confer kink resistance to the intracorporeal device upon bending. Embodiments of radial support members may include circumferential radial support members, helical radial support members and the like. The radial support members may be inflatable in some embodiments. By carefully selecting the size, configuration and spacing of the radial support members, kink resistance may be improved while the negative impact on other parameters of the intracorporeal device may be reduced.

Kink resistance is enhanced generally by decreasing the longitudinal spacing between radial support members; however, spacing that is too small may negatively impact the overall axial compliance of the device and may require excess fill material for device embodiments that include inflatable radial support members such as circumferential inflatable channels, helical inflatable channels or the like.

In one embodiment, a tubular intracorporeal device has a longitudinal section that includes a plurality of circumferential radial support members. There is a substantially constant longitudinal spacing between the circumferential radial support members that is about 50 to about 200 percent of a longitudinal thickness of the circumferential radial support members. A similar configuration may be used for a tubular intracorporeal device having a helical radial support member in addition to or in place of the plurality of circumferential radial support members.

In another embodiment, an endovascular graft section has a plurality of circumferential inflatable channels. The circumferential inflatable channels have a longitudinal spacing between a first segment of a first circumferential inflatable channel and an adjacent segment of a second circumferential inflatable channel that is about 50 to about 200 percent of a longitudinal thickness of the first segment. Some embodiments have a helical inflatable channel in addition to or in place of the plurality of circumferential inflatable channels with a longitudinal spacing between a first segment of the helical inflatable channel and an adjacent segment of the helical inflatable channel that is about 50 to about 200 percent of a longitudinal thickness of the first segment.

An embodiment may include an endovascular graft that has a first longitudinal section that includes a plurality of circumferential inflatable channels. There is a substantially constant longitudinal spacing between the circumferential inflatable channels in the first longitudinal section that is about 50 to about 75 percent of a longitudinal thickness of the circumferential inflatable channels with the circumferential inflatable channels in an inflated state. The endovascular graft also includes a second longitudinal section having a plurality of circumferential inflatable channels with a substantially constant longitudinal spacing between the circumferential inflatable channels. The substantially constant longitudinal spacing of the circumferential inflatable channels in the second longitudinal section is about 100 to about 200 percent of a longitudinal thickness of the circumferential inflatable channels with the circumferential inflatable channels in an inflated state. The substantially constant longitudinal spacing of the inflatable channels in each longitudinal section may be configured to substantially correspond to a likely bend radii of corresponding longitudinal sections of a patient's vascular or other conduit when the endovascular graft is in a deployed state within the patient's conduit. A similar configuration has a helical inflatable channel in place of or in addition to the circumferential inflatable channels.

In some embodiments, an endovascular graft may have longitudinal sections that are tubular. The longitudinal thickness of the circumferential inflatable channels or helical inflatable channel may be about 10 to about 30 percent of an outer transverse dimension of the tubular sections with the circumferential inflatable channel or helical inflatable channel in an expanded state. The inflatable channels may be inflated with an internal inflation pressure of about 3 to about 25 psi in some embodiments in order to provide compliance and maintain kink resistance.

These and other advantages of the invention will become more apparent from the following detailed description of the invention when taken in conjunction with the accompanying exemplary drawings.

BRIEF DESCRIPTION OF THE DRAWINGS

FIG. 1 is a schematic elevational view in longitudinal section of an endovascular graft having circumferential inflatable channels in fluid communication with a longitudinal inflatable channel.

FIG. 2 is a transverse cross sectional view of the endovascular graft of FIG. 1 taken along lines 2—2 in FIG. 1.

FIG. 3 is an elevational view of a model graft having a helical inflatable channel.

FIG. 4 shows a portion of the model graft of FIG. 3 in longitudinal section and illustrates the longitudinal thickness, longitudinal spacing and pitch of the coils of the helical inflatable channel.

FIG. 7 is an elevational view of the model graft prior to the initiation of stresses of a kinking simulation test.

FIG. 8 is an elevational view of the model graft after compression stress has been initiated on the model graft.

FIG. 9 is an elevational view of the model graft with a kink formed in the center portion of the model graft.

FIG. 10 is an elevational view in longitudinal section of the model graft in the kinked configuration of FIG. 9 and illustrates the restricted lumen in the center portion of the model graft.

DETAILED DESCRIPTION OF THE INVENTION

Figure 5:
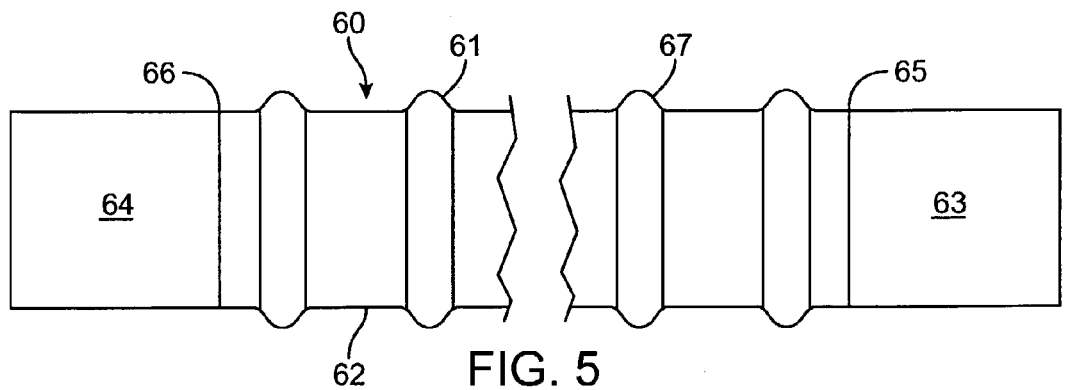
FIG. 5 shows a model graft having a plurality of circumferential inflatable channels with a relatively high longitudinal spacing.

FIGS. 1 and 2 schematically show an embodiment of an endovascular graft assembly 5. The endovascular graft assembly 5 has a graft body section 8 having a generally tubular configuration with a proximal portion 6, a distal portion 7, and circumferential radial support members in the form of circumferential inflatable channels 11 disposed on body section 8 and shown in an expanded state. The circumferential inflatable channels 11 are integrally formed in the body section 8 by seams 10 formed in the body section 8. A longitudinal inflatable channel 16 communicates with the circumferential inflatable channels 11.

A proximal connector member 12 may be embedded within multiple layers of graft body section 8 in the vicinity of graft body section proximal portion 6. A distal connector member 14 may also be embedded within multiple layers of graft body section 8 in the vicinity of graft body section distal portion 7.

One or more expandable members or stents (not shown) may be coupled or affixed to either or both proximal connector member 12 and distal connector member 14 via one or more connector member connector elements 17. Such expandable members or stents may serve to anchor the endovascular graft 5 within a body lumen such as a blood vessel and resist longitudinal or axial forces imposed on the endovascular graft 5 by the pressure and flow of fluids through the graft 5. In this embodiment, connector elements 17 of the proximal and distal connector members 12 and 14 extend longitudinally outside proximal portion 6 and distal portion 7 of endovascular graft assembly 5, respectively.

The circumferential inflatable channels 11 provide radial structural support to the tubular section or configuration of the body section 8. The circumferential inflatable channels may be filled on deployment of the graft with a variety of materials, including biocompatible fluids, such as saline or the like, or gels or fluids which are transmutable to a solid or semi-solid configuration. FIG. 2 illustrates a transverse cross sectional view of a circular inflatable channel 11 and longitudinal inflatable channel 16 of the graft assembly 5. Circular inflatable channel 11 generally has an annular configuration.

Referring again to FIG. 1, there is schematically shown in this embodiment a junction 18 between the distal portion 7 of graft assembly 5 and a distal portion 21 of graft assembly main body portion 22. There is also a junction 23 between the proximal portion 6 of graft assembly 5 and a proximal portion 24 of graft assembly main body portion 22. Junctions 18 and 23 may be tapered and also may have overlapping portions. Such junctions 18 and 23 may be secured by sintering or thermomechanical compaction of the flexible material of the junctions 18 and 23 if the flexible material used is a fusible material that may be secured to itself by processes such as seam formation with a heated stylus. Methods of seam forming as well as embodiments of seam forming devices as well as methods of forming and various embodiments of grafts and stent-grafts shown herein are described in co-pending and commonly owned U.S. patent application Ser. No. 10/029,557, entitled "Method and Apparatus for Manufacturing an Endovascular Graft Section", U.S. patent application Ser. No. 10/029,570, entitled "Method and Apparatus for Shape Forming Endovascular Graft Material", U.S. patent application Ser. No. 10/029,584, entitled "Endovascular Graft Joint and Method of Manufacture", by Chobotov et al., all of which were filed Dec. 20, 2001, U.S. patent application Ser. No. 10/327,711, entitled "Advanced Endovascular Graft", by Chobotov et al., filed Dec. 20, 2002, and PCT Application No. PCT/US02/40997, entitled "Method and Apparatus for Manufacturing an Endovascular Graft," by Chobotov et al., filed Dec. 20, 2002, the entirety of each of which are incorporated herein by reference. Other embodiments of devices incorporating features and methods described herein are disclosed in U.S. Pat. No. 6,395,019 (May 28, 2002) to Chobotov, the entirety of which is incorporated herein by reference.

An important function of inflatable channels, such as circumferential inflatable channels 11, in an endovascular graft may be to provide some kink resistance to the graft body section 8. Kink resistance of a tubular graft or portion or section thereof having circumferential inflatable channels 11 is generally a function of the inflation pressure of the circumferential inflatable channels 11, the longitudinal thickness of the inflatable channels 11, and the longitudinal spacing of the circumferential inflatable channels 11. Kinking in a vascular graft 5 or other tubular intracorporeal device or portion or section thereof generally occurs because the graft 5 is subjected to longitudinal compression, bending, or some combination thereof. There are many specific situations that may cause kinking. We have performed several studies to evaluate the relative effects of design parameters of endovascular grafts 5 and portions or sections thereof on kink resistance as described below.

Kink Resistance as a Function of Inflation Pressure

The geometry of a model graft 30 included in a kink simulation experiment is shown in FIG. 3. The model graft 30 includes a tubular section 31 and a helical inflatable channel 32, but does not include a proximal or distal inflatable cuff (each of which may have a large longitudinal thickness relative to that of the helical inflatable channel 32 since these components are not expected to play a significant role in kink resistance of the model graft 30). A small initial curvature in the shape of a half-sine wave has been incorporated into the model graft 30. The amplitude of the sine wave is nominally set at one percent of a transverse dimension of the model graft 30. This is a reasonable starting point for the simulation experiment as many if not all in vivo endovascular grafts typically will have some amount of longitudinal curvature imposed on them, depending on the indication for which they are used.

Proximal and distal rigid cylinders 33 and 34 are respectively attached to the proximal end 35 and distal end 36 of the model graft 30 as part of the simulation model. The distal rigid cylinder 34 is fixed in all degrees of freedom for the purposes of the simulation experiment, and the proximal rigid cylinder 33 is restrained from all translation and rotation except axial motion. An axial compression motion at a constant rate is prescribed for the proximal rigid cylinder 33 to introduce compression and buckling into the model graft 30. Single-surface contact is defined for the entire model graft 30 and outer surfaces of the helical inflatable channel 32 to properly model folding and prevent interpenetration of the model graft 30 surfaces during the simulation process.

As the model graft 30 is assumed to be constructed of multiaxially-expanded ePTFE for this study, an isotropic linear elastic material model was used to represent the mechanical behavior of graft 30 material. The material parameters used in this study were derived from a set of uniaxial tensile tests conducted by Vorp et al. at the University of Pittsburgh. The parameters obtained from these tests in two directions or orientations relative to fibril orientation of the ePTFE material were averaged and include an elastic modulus (E) of about 3.9 ksi and a Poisson's Ratio (υ) of about 0.05. A material thickness of 0.0078 in. (0.20 mm) was used for the regions of the model graft 30 outside of the helical inflatable channel 32 (i.e., the areas where six layers of ePTFE material were simulated), and a thickness of 0.0039 in. (0.01 mm) was used in the helical inflatable channel 32 walls since only three layers of ePTFE material were simulated in these areas. Although a linear elastic material model was used, the nonlinear formulation fully accounted for nonlinearities due to large displacements and large deformations, which play a significant role in the kink behavior of the model graft 30. In addition, single-surface contact algorithms were used to ensure no material interpenetration in the simulation and to correctly model the physics of the kink behavior.

Referring to FIG. 4, a longitudinal portion of the model graft 30 of FIG. 3 is shown in section. Outer layers of flexible material 37 are wrapped about inner layers of flexible material 38 with the helical inflatable channel 32 formed between the outer layers and inner layers 37 and 38. Various dimensions relating to the tubular section 31 and helical inflatable channel 32 are illustrated.

An outer transverse dimension or diameter of the tubular section 31 of the model graft 30 is indicated by arrowed line 39 and refers to the outer transverse dimension or diameter of the outer layers of the flexible material 37 of the tubular section 31 of the model graft 30 disposed between the coils 40 of the helical inflatable channel 32. The pitch of the helical inflatable channel 32 is indicated by arrowed line 41 and refers to the nominal dimension of the distance from a longitudinal center 42 of a coil of the helical inflatable channel 32 to a longitudinal center 45 of an adjacent coil of the helical inflatable channel 32. A longitudinal spacing of adjacent coils of the helical inflatable channel 32 is indicated by arrowed line 46 and indicates the minimum longitudinal distance from the outer layers of flexible material 37 of a coil of the helical inflatable channel 32 to the outer layers of flexible material 37 of a longitudinally adjacent coil of the helical inflatable channel 32.

A longitudinal thickness of the helical inflatable channel 32 is indicated by arrowed line 47 and a radial thickness of the helical inflatable channel is indicated by arrowed line 48. The longitudinal thickness of the helical inflatable channel 32 is the maximum longitudinal distance from the outer layer of flexible material 37 of a segment 51 of the helical inflatable channel 32 on one side of the helical inflatable channel 32 to the outer layers of flexible material 37 on the opposite side of the helical inflatable channel 32. The radial thickness 48 of the helical inflatable channel 32 is similarly defined in a radial direction from the outer layers of flexible material 37 to the inner layers of flexible material 38 of a segment 52 of the helical inflatable channel 32. A first segment 53 of the helical inflatable channel 32 is shown disposed longitudinally adjacent an adjacent second segment 54 of the helical inflatable channel 32.

Generally, the kink resistance simulation testing is performed as follows. First, hemodynamic pressure loads on the interior surface 55 of the model graft 30 and channel pressure loads on the interior surface 56 of the helical inflatable channel 32 are increased from zero to the predetermined values. A hemodynamic pressure of 120 mm Hg inside the tubular section 31 of the model graft 30 was used for all simulations. Once both pressure loads were up to their full predetermined values and the model graft 30 stabilized, then the proximal rigid cylinder 33 was given a prescribed inward axial motion to induce compression and buckling in the model graft 30. The simulation was performed using TriVascular, Inc.'s version of DYNA3D, an explicit nonlinear finite element code. These model graft 30 kink simulations were performed as transient dynamic analyses, with the loads applied sufficiently slowly that essentially quasi-static results were obtained.

A particular simulation study was conducted for the model graft 30 as shown in FIG. 3. For this study the model graft 30 parameters were: model graft 30 length of 4.0 in. (101.6 mm), model graft 30 lumen diameter of 0.87 in. (22.1 mm), helical inflatable channel 32 longitudinal thickness or diameter, 20 percent of model graft 30 lumen diameter, helical inflatable channel 32 pitch of 0.4 in. (10.2 mm), tubular section lumen hemodynamic pressure of 2.32 psi (120 mm Hg), and model graft 30 wall thickness of outer layers of flexible material 37 and inner layers of flexible material 38 of 0.006 in. (0.15 mm) outside the channels and 0.003 in. (0.08 mm) for the helical inflatable channel walls. For this study the distal end 36 of the model graft 30 was held fixed, and the proximal end 35 was held at a fixed diameter and restrained from rotation while being compressed axially. Kink resistance was tested for helical inflatable channel inflation pressures ranging from 0.1 psi to 25 psi.

Figure 6:
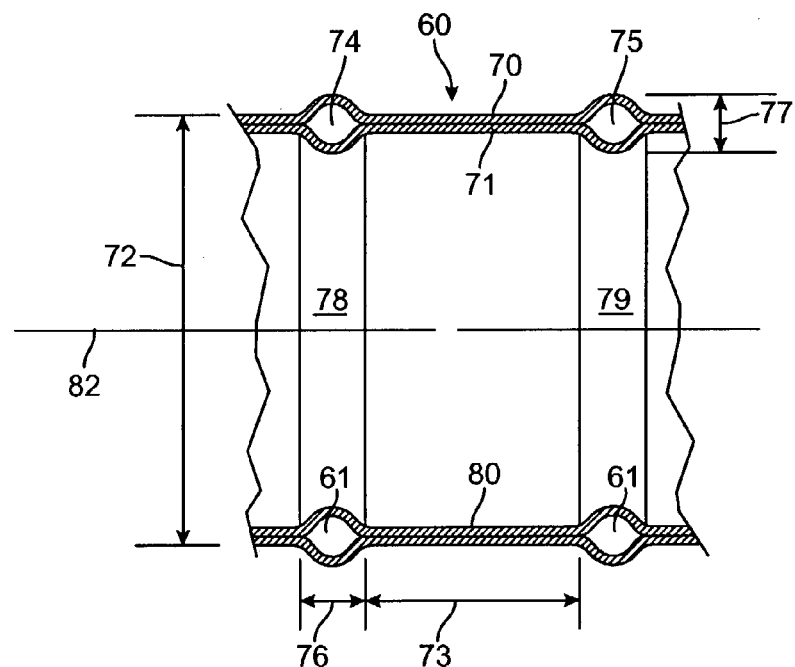
FIG. 6 shows a portion of the model graft of FIG. 5 and illustrates the longitudinal thickness and longitudinal spacing of the circumferential inflatable channels.
Figure 7:
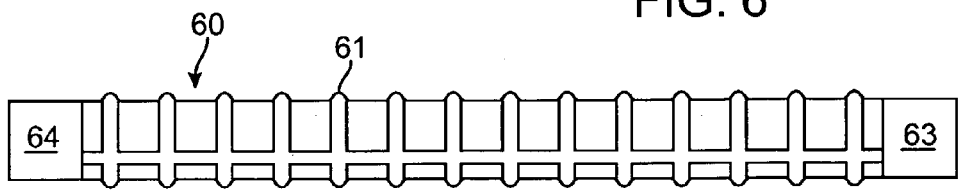
FIGS. 7–10 illustrate a sequence showing the results of a kink simulation test for the model graft of FIGS. 5 and 6.
Figure 8:
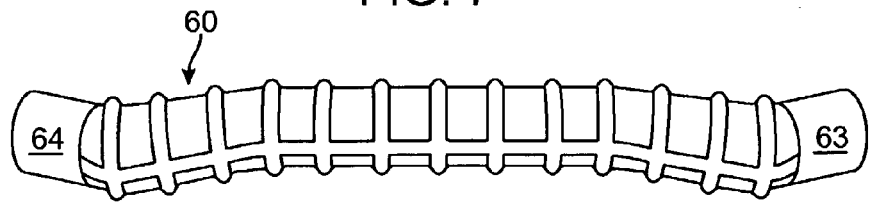

The same testing was performed on a model graft 60 having a plurality of circumferential inflatable channels 61 as seen on the model graft 60 shown in FIGS. 5 and 6. FIG. 5 illustrates a model graft 60 having a plurality of circumferential inflatable channels 61 disposed on a tubular section 62 of the model graft 60. The model graft 60 includes the tubular section 62 and a plurality of circumferential inflatable channels 61, but does not include a proximal or distal inflatable cuff (each of which may have a large longitudinal thickness relative to that of the circumferential inflatable channels 61 since these components are not expected to play a significant role in kink resistance of the model graft 60).

Proximal and distal rigid cylinders 63 and 64 are respectively attached to the proximal end 65 and distal end 66 of the model graft 60 as part of the simulation model. The distal rigid cylinder 64 is fixed in all degrees of freedom for the purposes of the simulation experiment, and the proximal rigid cylinder 63 is restrained from all translation and rotation except axial motion. An axial compression motion at a constant rate is prescribed for the proximal rigid cylinder 63 to introduce compression and buckling into the model graft 60.

Single-surface contact is defined for the entire model graft 60 and outer surfaces 67 of the circumferential inflatable channels 61 to properly model folding and prevent interpenetration of the model graft 60 surfaces during the simulation process. The design parameters such as model graft 60 length, tubular section 62 lumen diameter, circumferential inflatable channel 61 longitudinal thickness and longitudinal spacing of the circumferential inflatable channels 61 were the same as the corresponding parameters of the model graft 30 discussed above and shown in FIG. 3.

Referring to FIG. 6, a longitudinal portion of the model graft 60 of FIG. 5 is shown in section. Outer layers of flexible material 70 are shown wrapped about inner layers of flexible material 71 with the plurality of circumferential inflatable channels 61 formed between the outer layers 70 and inner layers 71. Various dimensions relating to the tubular section 62 and circumferential inflatable channels 61 are illustrated.

The outer transverse dimension of the tubular section 62 of the model graft 60 is indicated by arrowed line 72 and refers to the outer transverse dimension or diameter of the outer layers of the flexible material 70 of the tubular section 62 of the model graft 60 disposed between the circumferential inflatable channels 61. The longitudinal spacing of the circumferential inflatable channels 61 is indicated by arrowed line 73 and indicates the minimum longitudinal distance from the outer layers of flexible material 70 of a first circumferential inflatable channel 74 to the outer layers of flexible material 70 of a longitudinally adjacent circumferential inflatable channel 75.

The longitudinal thickness of the first circumferential inflatable channel 74 is indicated by arrowed line 76 and the radial thickness of the longitudinally adjacent circumferential inflatable channel 75 is indicated by arrowed line 77. The longitudinal thickness of the first circumferential inflatable channel 74 is the maximum longitudinal distance from the outer layer of flexible material 70 of a segment of the first circumferential inflatable channel 74 on one side of the first circumferential inflatable channel 74 to the outer layers of flexible material 70 on the opposite side of the circumferential inflatable channel 74. The radial thickness 77 of the adjacent circumferential inflatable channel 75 is similarly defined in a radial direction from the outer layers of flexible material 70 to the inner layers of flexible material 71 of a segment of the adjacent circumferential inflatable channel 75. A segment 78 of the first circumferential inflatable channel 74 is shown disposed longitudinally adjacent a segment 79 of a second circumferential inflatable channel 75.

Model graft 60 behavior at a 0.1 psi inflation pressure produced results comparable to an essentially unsupported endovascular graft. The predicted kink behavior for inflation pressures of 3, 10, and 25 psi were tested.

Figure 9:
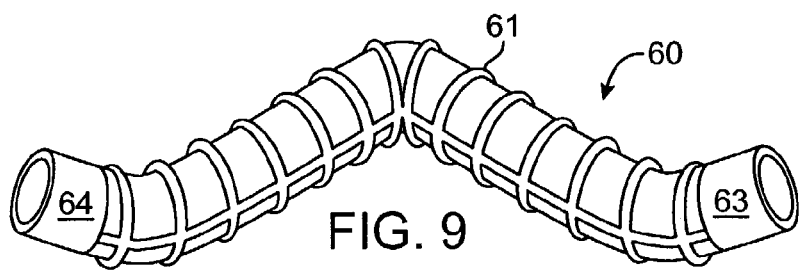
Figure 10:
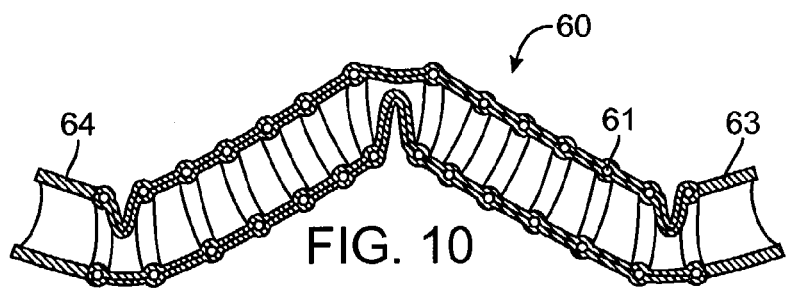

At low inflation pressures, the helical and circumferential channels 32 and 61 have little structural stability and collapse soon after coming into contact and going into compression as shown in the kinking sequence of FIGS. 7–10, wherein the model graft 60 of FIGS. 5 and 6 is subjected to a force and eventually kinks as shown in FIGS. 9 and 10. Low inflation pressures result in collapse of adjacent circumferential inflatable channels 61 after they come into contact on the inner radius of a model graft 60 subjected to bending. Collapse of circumferential inflatable channel 61 often results in the development of a kink at the location under contained compression, bending or both compression and bending. Higher inflation pressures provide more structural stability to the circumferential inflatable channels 61, which translates into greater kink resistance. Once a kink forms, a point of reduced lumen cross-sectional area is formed, as shown in FIG. 9 and more clearly in the longitudinal section view of the model graft 60 at FIG. 10. We have found that kink resistance of the model graft 60 markedly improves at 3 psi, and even more so at 10 psi inflation pressure.

At 25 psi inflation pressure, the circumferential channels 61 act as essentially rigid reinforcement structures, carrying the compressive load on the inner surface 80 of the bend of the model graft 60 without significant deformation. This high inflation pressure case is similar to the proposed inflation of the model graft 60 with an incompressible gel or liquid polymer that cross links to form a solid or semi-solid material.

Increasing inflation pressures above 25 psi appears to provide diminishing returns in the context of kink resistance and may actually adversely affect the sealing of circumferential inflatable channels 61 against the interior surface of a patient's body lumen or intracorporeal conduit, such as a vessel or an artery, having an irregular shape or cross section.

Kink Resistance as a Function of Longitudinal Channel Thickness and Spacing

A simulation study was conducted to investigate the kink resistance of model grafts having a configuration similar to that shown on the model graft 60 in FIG. 5. We investigated the effect of varying parameters such as longitudinal spacing and longitudinal thickness of the circumferential inflatable channels 61 of the model graft 60. In order to vary the longitudinal spacing of the circumferential inflatable channels 61, the length of model graft 60 was held constant and the number of circumferential inflatable channels 61 was increased and varied. In addition, when the longitudinal thickness of the circumferential inflatable channels 61 was varied, the longitudinal spacing between the circumferential inflatable channels was adjusted to maintain the original length of the model graft 60.

Two simulation schemes were used to evaluate the relative merit of the varied design parameters. A column compression/buckling analysis was conducted to observe the model graft buckling behavior and kink development. In this analysis each end of the model graft 60 was attached to rigid cylinders 63 and 64 as shown in FIG. 5. The cylinder motion was then prescribed to compress the model graft 60 with ends 65 and 66 of the model graft 60 left free to rotate. This provides a qualitative check on the graft behavior in compression loading. The second type of analysis was conducted by rotating each end 65 and 66 of the model graft 60 about a local axis to determine a minimum kink or bend radius for the model graft 60. In this analysis, the rigid cylinders 63 and 64 at the ends of the model graft 60 are given a prescribed rotation while they are also allowed to translate axially. As the ends 65 and 66 rotate, the model graft 60 forms a circular arc until a "critical" kink radius is achieved; i.e., a kink has initiated in the model graft 60. This approach allows for a quantitative assessment of the design parameters.

Generally, a dynamic relaxation method was used to impose an internal pressure loading of the model graft 60, followed by a transient dynamic simulation that either compressed or rotated the ends 65 and 66 of the model graft 60. The internal pressure of the circumferential inflatable channels 61 was specified to simulate a solid fill material. It was assumed that the gel within the circumferential inflatable channels 61 of the model graft 60 was "incompressible" and possessed a very low shear strength. The inflation gel was modeled using an isotropic-elastic-plastic material model with a low shear modulus (10 psi) and yield stress (10 psi), and a bulk modulus similar to that of water (500,000 psi).

The model graft 60 parameters used for this study were: model graft 60 length of 3.87 in. (98.30 mm), model graft 60 diameter of 0.39 in. (9.91 mm), lumen hemodynamic pressure 2.32 psi (120 mm Hg), and model graft 60 wall thickness of 0.006 in. (0.15 mm) between the circumferential inflatable channels 61 and 0.003 in. (0.08 mm) for the circumferential inflatable channel 61 walls. The number of circumferential inflatable channels 61 was varied from 14 to 21 (3.6 channels/in. to 5.4 channels/in.), while the longitudinal thickness or diameter of the circumferential inflatable channels 61 was varied from 0.080 to 0.126 in. (2.03 to 3.20 mm). A small initial curvature was introduced into the model graft 60; a half-sine wave shape with an amplitude of one percent of the model graft 60 length was used to provide some initial perturbation from a perfectly straight tubular section 62.

Kink resistance simulation testing was then performed on the various configurations of model graft 60. In one simulation, small circumferential inflatable channels 61 having a longitudinal thickness of about 0.08 in. (2.03 mm) were positioned on the tubular section 62 of the model graft 60 with a longitudinal spacing of about 0.212 in. (5.38 mm). These parameters give a longitudinal channel thickness to longitudinal spacing ratio of about 0.38. Another way to state this is that the longitudinal thickness of the circumferential inflatable channels 61 is about 38 percent of the longitudinal spacing of the circumferential inflatable channels 61 with the channels 61 in an inflated state. Note that a transverse section of the circumferential inflatable channels 61 taken along a longitudinal axis 82 of the model graft 60 has a substantially circular configuration such that the longitudinal thickness of the circumferential inflatable channels 61 is substantially the same as a radial thickness of the circumferential inflatable channels 61.

In a second simulation test, the model graft 60 tested had circumferential inflatable channels 61 with a longitudinal thickness and radial thickness of about 0.126 in. (3.20 mm). The circumferential inflatable channels 61 had a longitudinal spacing of about 0.162 in. (4.11 mm). This resulted in a longitudinal channel thickness to spacing ratio of about 78 percent.

These simulation tests did not show significant kink resistance for the model graft 60. Based on the results of these tests, our simulation estimated a minimum model graft 60 bend radius of about 10 mm for the first test described above. The second test described above, whose model graft 60 had an increased longitudinal thickness and decreased longitudinal spacing relative to the model used in the first simulation, does appear to yield slightly better kink resistance: our simulation estimated a minimum bend radius of about 8 mm for graft 60 under conditions imposed in the second simulation test.

For several subsequent simulation tests, the longitudinal spacing of the circumferential inflatable channels 61 of model graft 60 was further decreased to evaluate the effect of more closely spaced circumferential inflatable channels 61 on kink resistance. Overall, the ratio of longitudinal channel thickness to longitudinal spacing was varied from about 50 to about 200 percent. The kink resistance of the model graft 60 with reduced longitudinal spacing shows significant improvement over the relatively large longitudinal spacing cases discussed above in the first and second simulation tests, as the circumferential inflatable channels 61 provide some resistance to the collapsing of the column and the folding of material between the circumferential inflatable channels 61. For instance, our simulations estimated a minimum model graft 60 bend radius of about 4 to about 5 mm for spacing ratios from about 125 to about 200 percent as will be described later in conjunction with FIG. 14.

Figure 11:
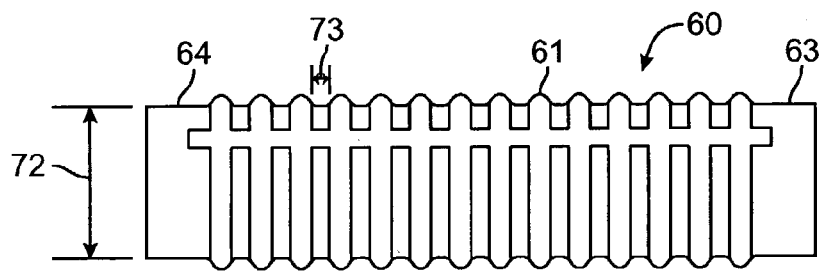
FIG. 11 illustrates an elevational view of a model graft having a relatively small longitudinal spacing between circumferential inflatable channels prior to the initiation of stresses from a kink simulation test.
Figure 12:
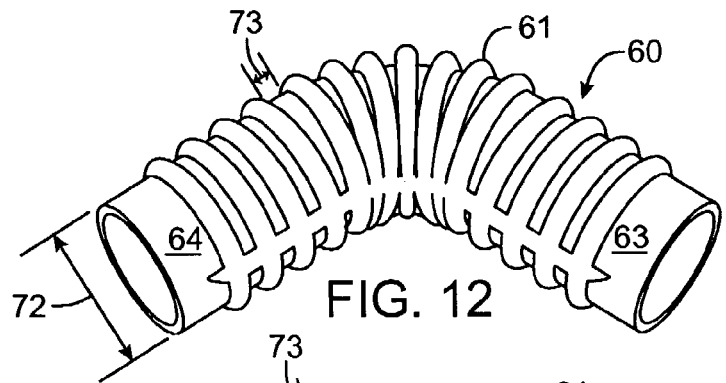
FIG. 12 illustrates the model graft of FIG. 11 after stresses of a kink simulation test have been imposed and shows the kink resistant nature of the model graft.
Figure 13:
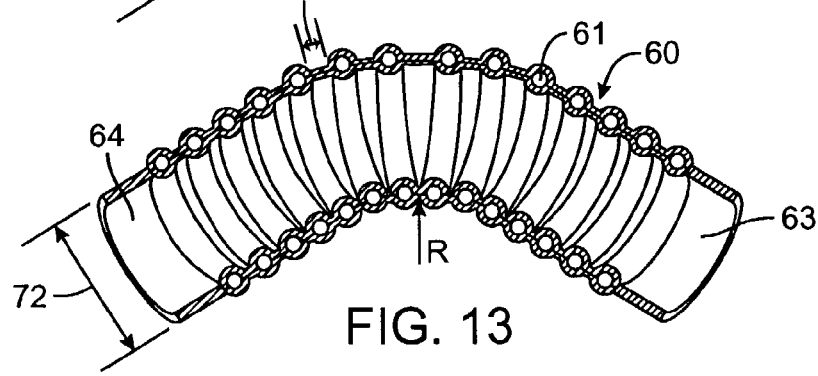
FIG. 13 shows the model graft of FIG. 12 in longitudinal section and illustrates the patency of the inner lumen of the model graft under the stresses and strains of the kink simulation test.

The effect of reducing longitudinal spacing 73 of the circumferential inflatable channels 61 in model graft 60 during such a simulation test may be seen in the exemplary illustrated sequence of FIGS. 11–13 (dimensions are not included to illustrate the general principle). A model graft 60 having a relatively small longitudinal spacing 73 between the circumferential inflatable channels 61 is subjected to deflections in a simulation test and the tubular section begins to deform as shown in FIGS. 11–12. However, the lumen of the tubular section remains patent even though the tubular section has been subjected to a small bend radius R shown in FIG. 13.

The axial length of the tubular section of the model graft 60 between the circumferential inflatable channels 61 of the model graft 60 has started to approach the longitudinal thickness of the circumferential inflatable channels 61; stated another way, the longitudinal channel thickness to spacing ratio approaches about 1.0. The resulting configuration provides resistance to slippage of circumferential inflatable channels 61 under adjacent circumferential inflatable channels 61 as the model graft 60 is compressed. A reduced longitudinal spacing allows the inflatable channels 61 to come into contact with nearly normal contact forces rather than the largely oblique contact forces which arise when the kink is more developed before circumferential inflatable channel 61 contact one another, such as occurs with increased longitudinal spacing.

Figure 14:
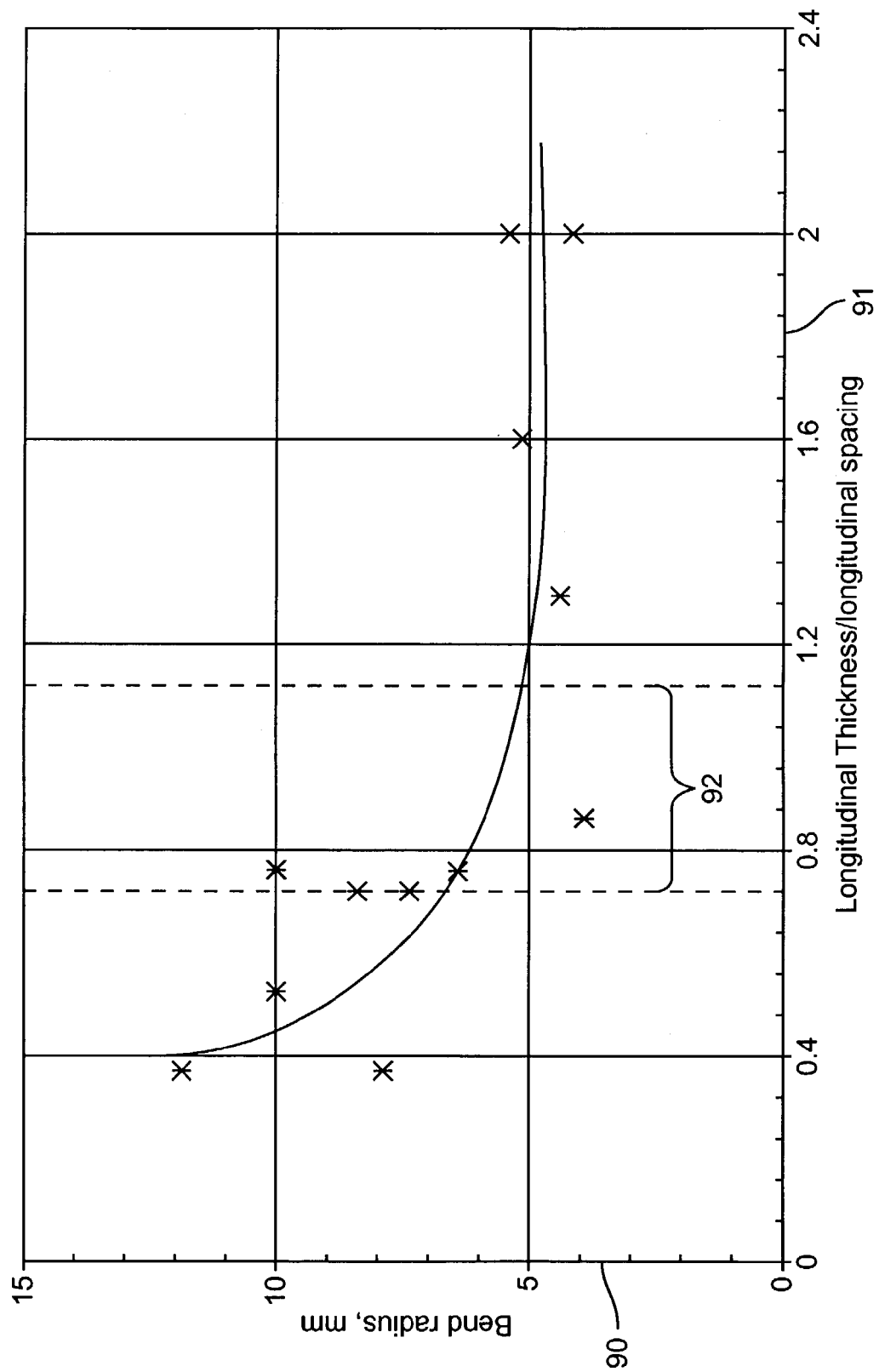
FIG. 14 is a graphical representation of data taken from kink simulation testing of model grafts having a plurality of circumferential inflatable channels with varied longitudinal spacing and varied longitudinal thickness. The "Y" axis represents the minimum bend radius for a given model graft configuration and the "X" axis represents the ratio of the longitudinal thickness of the circumferential inflatable channels of the model graft to the longitudinal spacing of the circumferential inflatable channels of the model graft.

FIG. 14 is a graphical representation of the results of several simulation tests such as those discussed above. The data represent the minimum bend radius that may be achieved for a model graft 60 without kinking plotted as a function of the ratio of longitudinal thickness of the model graft circumferential inflatable channels 61 to the longitudinal spacing for channels 61 that have a longitudinal or radial thickness of about 8.5 to about 32 percent of the outer transverse dimension or diameter of the model graft tubular section. The simulation test data represented in FIG. 14 include results from varied diameters of tubular section 62 of from about 10 mm to about 22.1 mm. It is generally desirable to reduce the number of circumferential inflatable channels 61 while improving the kink resistance of an endovascular graft or portion or section thereof, such as the endovascular graft 5 shown in FIG. 1 having circumferential inflatable channels 11.

A longitudinal spacing of circumferential inflatable channels 61 (or pitch of inflatable helical channel 32) that is too small may cause a variety of difficulties with regard to the manufacture, deployment and function of an endovascular graft 5 having these features. For example, unacceptably close longitudinal spacing 73 of circumferential inflatable channels 61 results in a large number of channels 61 that require a greater number of seams 10 to be formed in the tubular section 62. This increases the cost and complexity of manufacture of an endovascular graft 5. Increasing the number of circumferential inflatable channels 61 results in a greater internal inflatable volume of the circumferential inflatable channels 61 which must be filled with a fill fluid liquid, gel or gas upon deployment. This results in a greater amount of fill fluid used and greater amount of time required to fill the volume during deployment of the endovascular graft 5.

In addition, a large number of closely spaced circumferential inflatable channels 61 may cause a significant amount of axial contraction of the graft 5 as the circumferential inflatable channels 61 transition from a flat uninflated state to an inflated state where the longitudinal cross section has, for example, a substantially circular configuration. Significant axial contraction during deployment may create difficulties for the clinician deploying the graft 5, particularly with regard to properly sizing the graft for the patient's anatomy. Axial conformity or compressibility may also degrade with decreased longitudinal spacing between the circumferential inflatable channels 61.

The same or similar limitations would also apply to helical inflatable channels 32, as shown in FIGS. 3 and 4, where the pitch or longitudinal spacing between adjacent coils 40 is relatively small, creating the possibility for coil bind.

Referring again to FIG. 14, the "Y" axis 90 represents the minimum bend radius for a given model graft 60 configuration. The "X" axis 91 represents the ratio of the longitudinal thickness 76 of the circumferential inflatable channels 61 of the model graft 60 to the longitudinal spacing 73 of the circumferential inflatable channels 61 of the model graft 60. As can be seen from the results of kink resistance simulations plotted in the graphical format of FIG. 14, a longitudinal thickness of the circumferential inflatable channels 61 that is substantially equal to their longitudinal spacing (i.e. a ratio approaching about 1.0) produces a minimum bend radius of about 5 to about 7 mm. Clinical evaluations have shown this to be a desirable target for minimum bend radius given likely patient morphology for aortic aneurysms and the like.

In practice, we have found that channel thickness/spacing ratios of from about 0.5 and about 2.0, and more preferably from about 0.7 and about 1.1, yield these minimum bend radius parameters while also providing for acceptable manufacturability and axial compression behavior for endovascular grafts such as graft 5 of FIG. 1 as shown by the bracketed region 92 in FIG. 14. As can be appreciated, the thickness/spacing ratios illustrated in FIG. 14 and described in relation to FIGS. 11–13 are equally applicable to the grafts of FIGS. 3 and 4 that have a helical inflatable channel.

Thus, the simulation testing experiments discussed above indicate, and are confirmed by practical experience, that the ideal longitudinal thickness 76 of the circumferential inflatable channels 61 in an endovascular graft 5 or portion or section thereof should be from about 50 to about 200 percent of a longitudinal spacing 73 of the circumferential inflatable channels 61 (corresponding to a minimum bend radius of approximately 10 mm); more preferably from about 70 to about 110 percent (corresponding to a minimum bend radius of between about 5 and about 7 mm) for an endovascular graft with circumferential inflatable channels 61 that have a longitudinal or radial thickness that are about 8.5 to about 32 percent of the outer transverse dimension or diameter of the tubular section 62 of the model graft 60.

Figure 15:
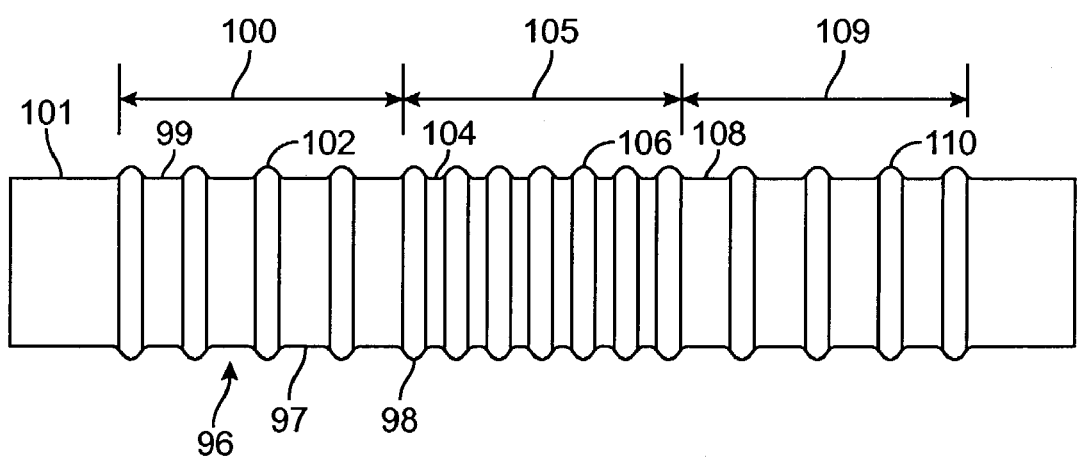
FIG. 15 shows a portion of an endovascular graft having a plurality of circumferential inflatable channels. The circumferential inflatable channels are disposed in three different longitudinal sections wherein the longitudinal spacing of the circumferential inflatable channels in each longitudinal section has a predetermined value that may be chosen to match a bend radius of a patient's intracorporeal conduit.

FIG. 15 shows a portion of a model graft 96 having a tubular section 97 with a plurality of circumferential inflatable channels 98 disposed on the tubular section 97. The circumferential inflatable channels 98 are disposed in three different longitudinal sections wherein the longitudinal spacing of the circumferential inflatable channels 98 in each longitudinal section has a predetermined value. The longitudinal spacing of the circumferential inflatable channels 98 may be chosen to substantially match a bend radius of a patient's intracorporeal conduit (not shown).

A first longitudinal section 99 indicated by arrowed line 100 is disposed at a first end 101 of the model graft 96 and has a plurality of circumferential inflatable channels 102 with a substantially constant longitudinal spacing. A second longitudinal section 104 indicated by arrowed line 105 has a plurality of circumferential inflatable channels 106 having a substantially constant longitudinal spacing that is less than the longitudinal spacing of the circumferential inflatable channels 102 of the first longitudinal section 99 of model graft 96. The second longitudinal section 104 is disposed axially adjacent the first longitudinal section 99 of the model graft 96. A third longitudinal section 108 indicated by arrowed line 109 is disposed axially adjacent the second longitudinal section 104. The third longitudinal section 108 has a plurality of circumferential inflatable channels 110 having a substantially constant longitudinal spacing that is greater than the longitudinal spacing of the circumferential inflatable channels 106 of the second longitudinal section 104 of the model graft 96.

In one embodiment, an endovascular graft may have a tubular section 97 with first longitudinal section 99 with a plurality of circumferential inflatable channels 102 with a substantially constant longitudinal spacing that is about 50 to about 75 percent of a longitudinal thickness of the circumferential inflatable channels 102 in the first longitudinal section 99 in an inflated state. The tubular section 97 also has a second longitudinal section 104 with a plurality of circumferential inflatable channels 106 with a substantially constant longitudinal spacing that is about 100 to about 200 percent of a longitudinal thickness of the circumferential inflatable channels 106 of the second longitudinal section 104 in an inflated state. The first longitudinal section 99 and second longitudinal section 104 may be axially adjacent each other.

In another embodiment, an endovascular graft may have a tubular section 97 with first longitudinal section 99 with a plurality of circumferential inflatable channels 102 with a substantially constant longitudinal spacing that is about 50 to about 75 percent of a longitudinal thickness of the circumferential inflatable channels 102 in the first longitudinal section 99 in an inflated state. The tubular section 97 also has a second longitudinal section 104 with a plurality of circumferential inflatable channels 106 with a substantially constant longitudinal spacing that is about 100 to about 200 percent of a longitudinal thickness of the circumferential inflatable channels 106 of the second longitudinal section 104 in an inflated state. The first longitudinal section 99 and second longitudinal section 104 may be axially adjacent each other. In this embodiment, the first longitudinal section 99 is configured to accommodate a conduit of a patient's anatomy that has a small bend radius down to about 8 mm. The second longitudinal section 104 is configured to accommodate a conduit of a patient's anatomy that has a bend radius of about 5 mm.

In another embodiment, an endovascular graft may have a tubular section 97 with a first longitudinal section 102 with a helical inflatable channel (such as the helical inflatable channel 32 shown in FIGS. 3 and 4) with a substantially constant longitudinal spacing between adjacent coils 40 that is about 50 to about 75 percent of a longitudinal thickness of the helical inflatable channel 32 with the helical inflatable channel 32 in an inflated state. The tubular section 97 has a second longitudinal section 104 with a helical inflatable channel 32 with a substantially constant longitudinal spacing between adjacent coils 40 with the helical inflatable channel 32 in an inflated state. The longitudinal spacing of the coils 40 of the second longitudinal section 104 may be about 100 to about 200 percent of a longitudinal thickness of the helical inflatable channel 32 of the second longitudinal section 99 in an inflated state.

For ease of reference, the above illustrations and discussions of the graft sections focused on uniaxial or tubular endovascular graft assemblies 5. As can be appreciated, however, the concepts of the present invention are equally applicable to graft sections that are on any portion of bifurcated endovascular graft assemblies. Some non-limiting examples of bifurcated graft assemblies are shown and described in commonly owned U.S. patent application Ser. No. 10/029,559, entitled "Advanced Endovascular Graft," filed on Dec. 20, 2001 by Chobotov et al., and U.S. patent application Ser. No. 10/327,711, entitled "Advanced Endovascular Graft," filed on Dec. 20, 2002 by Chobotov et al., the complete disclosures of which are incorporated herein by reference.

While particular forms of embodiments of the invention have been illustrated and described, it will be apparent that various modifications can be made without departing from the spirit and scope of the invention. Accordingly, it is not intended that the invention be limited, except as by the appended claims.

What is claimed is:

1. An endovascular graft comprising a longitudinal section which comprises a plurality of circumferential inflatable channels with a substantially constant longitudinal spacing between the circumferential inflatable channels that is about 50 to about 200 percent of a longitudinal thickness of the circumferential inflatable channels when the circumferential inflatable channels are in an inflated state.

2. The endovascular graft of claim 1 wherein the circumferential inflatable channels are in an inflated state.

3. The endovascular graft of claim 1 wherein a transverse cross section of the circumferential inflatable channels has a substantially annular configuration when the circumferential inflatable channels are in an inflated state.

4. The endovascular graft of claim 1 wherein the longitudinal section comprises a tubular section and a longitudinal thickness of the circumferential inflatable channels is about 10 to about 30 percent of an outer transverse dimension of the tubular section when the circumferential inflatable channels are in an inflated state.

5. The endovascular graft of claim 1 wherein the substantially constant longitudinal spacing between the circumferential inflatable channels is about 70 to about 110 percent of a longitudinal thickness of the circumferential inflatable channels when the circumferential inflatable channels are in an inflated state.

6. The endovascular graft of claim 1 wherein the longitudinal section comprises a tubular section and the circumferential inflatable channels are formed integrally with a flexible material of the tubular section.

7. The endovascular graft of claim 1 wherein the longitudinal section comprises a tubular section and the circumferential inflatable channels are formed separately from the tubular section and secured thereto.

8. The endovascular graft of claim 1 wherein a longitudinal section of the circumferential inflatable channels has a substantially round configuration when the circumferential inflatable channels are in an inflated state.

9. The endovascular graft of claim 1 wherein a longitudinal section of the circumferential inflatable channels has a substantially round configuration when the circumferential inflatable channels are in an inflated state.

10. A tubular endovascular graft comprising a longitudinal section which comprises a helical inflatable channel with a substantially constant longitudinal spacing between adjacent coils of the helical inflatable channel that is about 50 to about 200 percent of a longitudinal thickness of the helical inflatable channel when the helical inflatable channel is in an inflated state.

11. The endovascular graft of claim 10 wherein the helical inflatable channel is in an inflated state.

12. The endovascular graft of claim 10 wherein the longitudinal section comprises a tubular section and a longitudinal thickness of the helical inflatable channel is about 10 to about 30 percent of an outer transverse dimension of the tubular section when the helical inflatable channel is in an inflated state.

13. The endovascular graft of claim 10 wherein the substantially constant longitudinal spacing between adjacent coils of the helical inflatable channel that is about 70 to about 110 percent of a longitudinal thickness of the helical inflatable channel when the helical inflatable channel is in an inflated state.

14. The endovascular graft of claim 10 wherein the longitudinal section comprises a tubular section and the helical inflatable channel is formed integrally with a flexible material of the tubular section.

15. The endovascular graft of claim 10 wherein the longitudinal section comprises a tubular section and the helical inflatable channel is formed separately from the tubular section and secured thereto.

16. An endovascular graft comprising:
a) a first longitudinal endovascular graft section which comprises a plurality of circumferential inflatable channels with a substantially constant longitudinal spacing between the circumferential inflatable channels that is about 50 to about 75 percent of a longitudinal thickness of the circumferential inflatable channels with the circumferential inflatable channels in an inflated state; and
b) a second longitudinal endovascular graft section which comprises a plurality of circumferential inflatable channels with a substantially constant longitudinal spacing between the circumferential inflatable channels that is about 100 to about 200 percent of a longitudinal thickness of the circumferential inflatable channels of the second longitudinal section with the circumferential inflatable channels in an inflated state.

17. The endovascular graft of claim 16 wherein the longitudinal spacing of the circumferential inflatable channels of the first and second longitudinal sections is configured to substantially correspond to a bend radii of corresponding longitudinal sections of a patient's vascular conduit upon deployment.

18. The endovascular graft of claim 16 wherein the first and second longitudinal sections comprise tubular sections and a longitudinal thickness of the circumferential inflatable channels is about 10 to about 30 percent of an outer transverse dimension of the tubular sections with the circumferential inflatable channel in an expanded state.

19. The endovascular graft of claim 16 wherein the first longitudinal section is axially adjacent the second longitudinal section.

20. An endovascular graft comprising:
a) a first longitudinal endovascular graft section which comprises a helical inflatable channel with a substantially constant longitudinal spacing between coils of the helical inflatable channel that is about 50 to about 75 percent of a longitudinal thickness of the helical inflatable channel with the helical inflatable channel in an inflated state; and
b) a second longitudinal endovascular graft section which comprises a helical inflatable channel with a substantially constant longitudinal spacing between coils of the helical inflatable channel that is about 100 to about 200 percent of a longitudinal thickness of the helical inflatable channel of the second longitudinal section with the circumferential inflatable channels in an inflated state.

21. The endovascular graft of claim 20 wherein the longitudinal spacing of each longitudinal section is configured to substantially correspond to a bend radii of corresponding longitudinal sections of a patient's vascular conduit upon deployment of the endovascular graft.

22. The endovascular graft of claim 20 wherein the first and second longitudinal sections comprise tubular sections and wherein a longitudinal thickness of the helical inflatable channel is about 10 to about 30 percent of an outer transverse dimension of the tubular sections with the helical inflatable channel in an expanded state.

23. The endovascular graft of claim 20 wherein the first longitudinal section is axially adjacent the second longitudinal section.

24. An endovascular graft comprising:
an endovascular graft section, the endovascular graft section comprising:
a plurality of circumferential inflatable channels having a longitudinal spacing between a first segment of a first circumferential inflatable channel and an adjacent segment of a second circumferential inflatable channel that is about 50 to about 200 percent of a longitudinal thickness of the first segment when the first segment is in an expanded state.

25. The endovascular graft of claim 24 wherein the endovascular graft section comprises a tubular section and the circumferential inflatable channels are integrally formed with the tubular section.

26. The endovascular graft of claim 24 wherein the endovascular graft section comprises a tubular section and the circumferential inflatable channels are formed separately from the tubular section and secured to the tubular section.

27. The endovascular graft of claim 24 wherein the circumferential inflatable channels are in an inflated state with an internal inflation pressure of about 3 to about 25 psi.

28. The endovascular graft of claim 24 wherein the endovascular graft section comprises a tubular section and the tubular section is comprised of a flexible material.

29. The endovascular graft of claim 28 wherein the flexible material comprises ePTFE.

30. The endovascular graft of claim 24 wherein the endovascular graft section comprises a tubular section and a longitudinal thickness of the circumferential inflatable channels is about 10 to about 28 percent of an outer transverse dimension of the tubular section with the circumferential inflatable channels in an expanded state.

31. The endovascular graft of claim 24 wherein the longitudinal thickness of the circumferential inflatable channels in the graft section is substantially the same.

32. The endovascular graft of claim 31 wherein the longitudinal spacing between adjacent segments of the circumferential inflatable channels in the graft section is substantially the same.

33. An endovascular graft comprising:
an endovascular graft section, the endovascular graft section comprising:
a helical inflatable channel having a longitudinal spacing between a first segment of the helical inflatable channel and an adjacent second segment of the helical inflatable channel disposed longitudinally from the first segment that is about 50 to about 200 percent of a longitudinal thickness of the first segment when the helical inflatable channel is in an expanded state.

34. The endovascular graft of claim 33 wherein the endovascular graft section comprises a tubular section and the helical inflatable channel is integrally formed with the tubular section.

35. The endovascular graft of claim 33 wherein the endovascular graft section comprises a tubular section and the helical inflatable channel is formed separately from the tubular section and secured to the tubular section.

36. The endovascular graft of claim 33 wherein the helical inflatable channel is in an inflated state with an internal inflation pressure of about 5 to about 20 psi.

37. The endovascular graft of claim 33 wherein the endovascular graft section comprises a tubular section and the tubular section is comprised of a flexible material.

38. The endovascular graft of claim 37 wherein the flexible material comprises ePTFE.

39. The endovascular graft of claim 33 wherein the endovascular graft section comprises a tubular section and a longitudinal thickness of the helical inflatable channel is about 10 to about 30 percent of an outer transverse dimension of the tubular section with the helical inflatable channel in an expanded state.

40. The endovascular graft of claim 33 wherein the longitudinal thickness of the helical inflatable channel in the graft section is substantially the same.

41. The endovascular graft of claim 40 wherein the longitudinal spacing between adjacent segments of the helical inflatable channel in the graft section is substantially the same.

* * * * *